United States Patent [19]

Flashinski et al.

[11] Patent Number: 4,774,081

[45] Date of Patent: Sep. 27, 1988

[54] CONTACT INSECT REPELLENTS

[75] Inventors: Stanley J. Flashinski; John H. Hainze; Calvin J. Verbrugge, all of Racine County, Wis.

[73] Assignee: S. C. Johnson & Son, Inc., Racine, Wis.

[21] Appl. No.: 2,904

[22] Filed: Jan. 13, 1987

[51] Int. Cl.$^4$ .............................................. A61K 31/78
[52] U.S. Cl. ............................. 424/78; 424/DIG. 10; 514/919
[58] Field of Search ...................... 424/78, 81, 83, 405, 424/DIG. 10; 514/919

[56] References Cited

U.S. PATENT DOCUMENTS

| | | | |
|---|---|---|---|
| 2,808,359 | 10/1957 | Schmutzler | 514/533 |
| 2,884,355 | 4/1959 | Goodhue et al. | 514/354 |
| 4,358,573 | 11/1982 | Verbrugge | 526/272 |
| 4,435,383 | 3/1984 | Wysong | 424/78 |
| 4,489,056 | 12/1984 | Himmelstein et al. | 424/486 |
| 4,548,764 | 10/1985 | Munteanu et al. | 261/75 |
| 4,663,346 | 5/1987 | Coulston et al. | 514/456 |
| 4,747,902 | 5/1988 | Saitoh | 156/244.11 |

OTHER PUBLICATIONS

Mehr et al., J. Am. Mosq. Control Assoc. 1(2): 143–147 (Jun. 1985), Laboratory Evaluation of Controlled-Release Insect Repellent Formulations.

Randall & Brower, J. Med. Entomol, 23(3): 251–255 (May 1986), A New Method to Determine Repellent, Neutral, or Agregative Properties of Chemicals on *Blattella germanica* (Dictyoptera:Blattellidae).

*Primary Examiner*—John F. Terapane
*Assistant Examiner*—Catherine S. Kilby

[57] ABSTRACT

This invention relates to volatile contact insect repellent compositions comprising an insect repellent, such as deet or butyl hydroxy anisole, and specific maleic anhydride/alpha olefin polymers to increase the residual activity of the insect repellent.

29 Claims, No Drawings

CONTACT INSECT REPELLENTS

BACKGROUND OF THE INVENTION

This application is related to a copending application entitled "Improved Volatile Insect Repellents" and filed concurrently herewith.

This invention relates to new and useful compositions of matter suitable as contact insect repellents. More particularly, this invention relates to the use of maleic anhydride/alpha olefin polymers to increase the residual activity of contact insect repellents.

Volatile contact insect repellents have the disadvantage of giving protection only for relatively short periods of time due to their rapid evaporation and/or absorption by the treated substrate. Both problems, absorption and evaporation, necessitate frequent applications which are bothersome and time-consuming.

Adding adjuvant materials to increase the persistence of insect repellents was reported as early as 1928 for a formula consisting of oil of citronella, spirits of camphor, oil of tar, oil of pennyroyal and castor oil. Mehr et al., Laboratory Evaluation of Controlled-Release Insect Repellent Formulations, *J. Am. Mosq. Control Assoc.*, Vol. 1(2):143 (June, 1985). The Mehr et al. researchers tested the persistence of several controlled-release formulations of diethyl toluamide, or more specifically, N,N-diethyl-3 methylbenzamide. Diethyl toluamide is commonly known as deet. These formulations consisted of microcapsule and free-repellent formulations containing hydrophilic vinyl polymers, such as polyvinylpyrrolidone.

U.S. Pat. No. 2,808,359 discloses that absorption by the skin and evaporation are reduced by mixing insect repellents with hydroxyalkyl esters of dicarboxylic acids, including bis(2-ethyl-3 hydroxy-hexyl) maleate. Other patents also disclose the use of various materials to extend the residual activity of insect repellents or slow release pesticides. See, for example, U.S. Pat. Nos. 2,884,355, 4,435,383 and 4,489,056.

U.S. Pat. No. 4,358,573 teaches that maleic anhydride/alpha olefin polymers are useful as mold release agents, slip agents and additives to floor polishes. They are not said to increase the residual activity of volatile contact insect repellents.

Accordingly, a long-standing need exists to provide a volatile contact insect repellent composition for surface application with improved residual activity, i.e., the period of repellent activity after application.

SUMMARY OF THE INVENTION

In a first embodiment, this invention relates to volatile contact insect repellent compositions having enhanced residual insect repellent activity comprising: (1) at least one volatile contact insect repellent; and (2) at least one polymer consisting of (a) about 49–60 mole percent maleic anhydride, and (b) about 51–40 mole percent of at least one 1-olefin having 4–30+ carbon atoms, wherein said polymer is present in sufficient amounts to provide enhanced residual activity and effective insect repellency. The preferred weight ratio of insect repellent to polymer is about 5:1 to about 50:1. Additionally, this invention relates to a method of repelling insects utilizing these polymer-containing volatile contact insect repellent compositions.

In a second embodiment, this invention incudes compositions having enhanced residual insect repellency comprising: (1) at least one volatile contact insect repellent; and (2) at least one polymer consisting of (a) about 49–60 mole percent maleic anhydride, (b) about 10–40 mole percent of at least one 1-alkene having from 4–16 carbon atoms, and (c) about 10–40 mole percent of at least one 1-alkene having at least 18–30+ carbon atoms, wherein said polymer is present in sufficient amounts to provide enhanced residual activity and effective insect repellency. Unless otherwise stated, references to mole percents are based on the total weight of the polymer.

In still further embodiments, the above compositions may optionally contain various alcohols, such as the lower alkanols, ethanol and the like, or other solvents and/or propellents, if an aerosol formulation is desired.

It is believed that the compositions of the present invention and the method of using them unexpectedly prolong residual activity by reducing absorption to the treated substrate and evaporation of the insect repellent.

It has been found that the compositions of the invention and the methods of using them unexpectedly prolong residual activity against cockroaches as compared with those formulations not containing a polymer of the invention.

DESCRIPTION OF THE PREFERRED EMBODIMENTS

The volatile contact insect repellents that may be utilized in accordance with the teachings of this invention are those considered effective against the particular insect targeted.

Examples of volatile contact insect repellents effective against cockroaches and other crawling insects that are repelled by contact or tactile sensory perceptions include: N,N-diethyl toluamide (deet); citronellal (3,7-dimethyl-6-octenal); citronellol (3,7-dimethyl-6-octen-1-ol); geraniol (trans-3,7-dimethyl-2,6-octadien-1-ol); nerol (cis-3,7-dimethyl-2,6-octadien-1-ol); linalool (3,7-dimethyl-1-6,-octadien-1-ol); butyl hydroxy anisole; and mixtures thereof.

The concentration of contact insect repellent utilized in accordance with the teachings of this invention is not critical. The lower limit is defined by that amount required for an effective dosage, and the upper limit, by economic considerations. The amount of insect repellent employed will vary depending on several factors, including, the type of contact insect repellent, the targeted insect or insects, and the other ingredients utilized, e.g., the maleic anhydride polymer.

The concentration of insect repellent can preferably be from about 1% to 90%, based on the total weight of the insect repellent composition. The preferred ranges are from about 1 to 25 percent, based on the total weight of the insect repellent composition. Unless otherwise indicated, all percentages of ingredients are calculated as weight percentages based on the total weight of the contact insect repellent composition.

Other volatile contact insect repellents, especially those well known in the art and useful for such purposes, can also be readily utilized.

Maleic anhydride/alpha olefin polymers may be utilized, in accordance with the teachings of this invention, to increase the residual activity of volatile contact insect repellents. These polymers include compositions having (a) about 49 to 60 mole percent maleic anhydride and (b) about 51 to 40 mole percent of at least one 1-alkene having from 4–30+ carbon atoms. Preferred maleic anhydride polymers have (a) about 49–55 mole percent maleic anhydride and (b) about 45–51 mole percent of at least one 1-alkene having from 6-16 carbon atoms (e.g. 1-decene), with 8-12 carbon atoms being more preferred. A more preferred polymer has about 50 mole percent maleic anhydride and about 50 mole 1-decene.

Additional polymers that may be utilized in accordance with the teachings of this invention include the maleic anhydride alpha olefin terpolymers disclosed in U.S. Pat. No. 4,358,573, which is incorporated herein by reference. These are formed from monomers comprising: (a) about 49-60 mole percent maleic anhydride, (b) about 10-40 mole percent of at least one 1-alkene having from 4-16 carbon atoms, and (c) about 10-40 mole percent of at least one 1-alkene having from 18-30+ carbon atoms.

Additionally, preferred maleic anhydride/alpha olefin polymers include: (a) about 49-55 mole percent maleic anhydride, (b) about 20-30 mole percent of at least one 1-alkene having from 8-12 carbon atoms (e.g. 1-decene), and (c) about 20-30 mole percent of at least one 1-alkene having from 18 to 24 carbon atoms (1-octadecene); and also (a) about 49-55 mole percent maleic anhydride, (b) about 20-30 mole percent of at least one 1-alkene having from 8-12 carbon atoms, and (c) about 20-30 mole percent of a mixture of 1-alkenes consisting of about 45-55 mole percent 1-eicosene, about 40-55 mole percent 1-docosene, and about 5-10 mole percent 1-tetracosene.

The maleic anhydride/alpha olefin polymers are generally present in amounts sufficient to reduce the evaporation and absorption of the volatile contact insect repellent, i.e., to provide enhanced residual activity and maintain an effective insect repellency. Accordingly, these materials may be present in amounts from about 1 to 25 percent, based on the total weight of the insect repellent composition, with preferred amounts ranging from about 1 to 5 percent.

A preferred weight ratio of insect repellent to polymer of at least about 5:1 to about 50:1 is desirable to attain the objectives of this invention. The particular ratio selected is of course, dependent on the repellent, its volatility and the polymer utilized. If the ratio of repellent to polymer is less than about 5:1, however, the polymer may prevent the targeted insect from contacting the insect repellent, and thereby hindering repellency. If the ratio is greater than about 50:1, the volatile repellent will usually be released too rapidly and the composition will quickly lose its residual activity.

The application of these compositions to various substrates is facilitated by solution of the active ingredients in solvents, such as the lower alkanols, ethanol and the like, kerosene and similar petroleum oils, ethers, ketones, aldehydes and the like.

Additionally the compositions of the present invention may be applied in aerosol form, in which case, the above-identified compositions may additionally contain a propellent or a mixture of propellents. The type of propellent is not critical, and any of those generally utilized can be employed to produce an aerosol formula. Typical propellents include isobutane, propane, n-butane, and the like, and mixtures thereof, which are utilized in conventional amounts.

In preparing the compositions of this invention, the insect repellent is generally added directly to an alcoholic polymer solution, which can then be formulated or packaged in any form commonly used for such repellents, i.e., aerosol, pump spray, roll-on or lotion. It is clear to those skilled in the art that the anhydride group of the polymer is converted to the half alkyl ester under these conditions, i.e., the presence of alcohol at room temperature.

In each of the following formulations, $MA_N$=maleic anhydride. The number or numerical range preceeding $MA_N$ is the mole percent of maleic anhydride in the polymer. The $C_x$—$C_{x'}$ group denotes the number of carbon atoms comprising the 1-alkene, and the number or numerical range preceeding this designation is the mole percent of the 1-alkene in the polymer.

Typical preparations of this invention include:

| Ingredients | Amount (percent by weight) | |
|---|---|---|
| | Preferred | More Preferred |
| General Formula | | |
| Insect repellant | 1-90 | 1-25 |
| Polymer | 1-25 | 1-5 |
| Carrier/propellent | 0-99 | 70-98 |

| Ingredients | Amount* | Repellent: Polymer Ratio |
|---|---|---|
| Formula 1 | | |
| Deet | 1-50 | |
| 49-60 $MA_N$/51-40 $C_8$-$C_{12}$ | 1-5 | 5:1 to 50:1 |
| Carrier/propellent | 45-98 | |
| Formula 2 | | |
| Deet | 1-25 | |
| 49-60 $MA_N$/51-40 $C_8$-$C_{12}$ | 1-5 | 5:1 to 25:1 |
| Carrier/propellent | 70-98 | |

| Ingredients | Amount | | Repellent: Polymer Ratio |
|---|---|---|---|
| | 3A | 3B | |
| Formula 3 | | | |
| Deet | 5 | 20 | |
| 50 $MA_N$/50 $C_{10}$ | 1 | 4 | 5:1 |
| Carrier/propellent | 94 | 76 | |

| Ingredients | Amount | Repellent: Polymer Ratio |
|---|---|---|
| Formula 4 | | |
| Deet | 1-50 | |
| 49-55 $MA_N$/20-30 $C_8$-$C_{12}$ 20-30 $C_{18}$-$C_{24}$ | 1-5 | 5:1 to 50:1 |
| Carrier/propellent | 45-98 | |
| Formula 5 | | |
| Deet | 1-25 | |
| 49-55 $MA_N$/20-30 $C_8$-$C_{12}$ 20-30 $C_{18}$-$C_{24}$ | 1-5 | 5:1 to 25:1 |
| Carrier/propellent | 70-98 | |

| Ingredients | Amount | | Repellent: Polymer Ratio |
|---|---|---|---|
| | 6A | 6B | |
| Formula 6 | | | |
| Deet | 5 | 20 | |
| 50 $MA_N$/25 $C_{10}$ 25 $C_{18}$ | 1 | 4 | 5:1 |
| Carrier/propellent | 84 | 76 | |

| Ingredients | Amount | Repellent: Polymer Ratio |
|---|---|---|
| Formula 7 | | |
| Deet | 1-50 | |
| 49-55 $MA_N$/20-30 $C_8$-$C_{12}$ 20-30 $C_{20}$-$C_{24}$ | 1-5 | 5:1 to 50:1 |
| Carrier/propellent | 45-98 | |
| Formula 8 | | |
| Deet | 1-25 | |
| 49-55 $MA_N$/20-30 $C_8$-$C_{12}$ 20-30 $C_{20}$-$C_{24}$ | 1-5 | 5:1 to 25:1 |
| Carrier/propellent | 70-98 | |

| Ingredients | Amount | | Repellent: Polymer Ratio |
|---|---|---|---|
| | 9A | 9B | |
| Formula 9 | | | |
| Deet | 5 | 20 | |
| 49-55 $MA_N$/25 $C_{10}$ | 1 | 4 | 5:1 |

-continued

| Ingredients | Amount | |
|---|---|---|
| 25 $C_{20}$-$C_{24}$*** | | |
| Carrier/propellent | 94 | 76 |

| Ingredients | Amount | Repellent: Polymer Ratio |
|---|---|---|
| Formula 10 | | |
| Deet | 1-25 | |
| 49-55 $MA_N$/20-30 $C_{8-12}$ | 1-5 | 5:1 to 25:1 |
| 20-30 $C_{24-30}$ | | |
| Carrier/propellent | 70-98 | |

*All amounts are given as weight percentages of the total composition.
**The $C_{20}$-$C_{24}$ 1-alkenes comprise 45-55 mole percent $C_{20}$, 40-50 mole percent $C_{22}$ and 5-10 mole percent $C_{24}$.
***The $C_{20}$-$C_{24}$ 1-alkenes comprise 50.1 mole percent $C_{20}$, 43.4 mole percent $C_{22}$ and 6.5 mole percent $C_{24}$.

Butyl hydroxy anisole, as well as the other volatile contact insect repellents disclosed herein, may be substituted for deet in Formulas 1-10 above. In order to illustrate the improved results obtained from the present invention, repellency tests were conducted to show the improvements in residual activity provided by the volatile contact insect repellent compositions of the present invention. These tests, which illustrate the scope of the invention but do not limit it, were carried out in the following manner:

EXAMPLE 1

Deet has been discovered to be a good repellent for German cockroaches, but lacking in functional residual repellent activity. To test the residual activity of the formulations of this invention, deet as mixed with the polymers shown in Tables 1 and 2, and tested for cockroach repellency in accordance with the method disclosed in J. B. Randall and D. O. Bower, "A New Method to Determine Repellent, Neutral, or Aggregative Properties of Chemicals on *Blattella Germanica* (Dictyoptera: Blattellidae)", *J. Med. Entomol.*, Vol. 23(3): 251-255 (May, 1986).

All formulas in Table 1 were supplied as aerosols. Test plates were sprayed with the respective formulation to provide complete and even coverage of the test plates. Ten adult male and ten adult female cockroaches were used in each experiment, which was replicated 5 times.

The test plates treated with the respective formulations were exposed to cockroaches in the experiments at 0, 1, 4, 7, 14 and 21 days after treatment. Except for the 0 day experiments, treated test plates were stored until exposure to insects in the experimental situation.

The Table 2 formulas were tested for cockroach repellency by the same method described above. Two levels of deet were combined with two levels of polymer to make up these aerosol test formulas, with the results determined from 18 observations of 5 replications.

TABLE 1

| Formula | Ingredients and Concentration[1] | Repellency Effect Against German Cockroaches[2] |
|---|---|---|
| Control-1 | 5% deet<br>5% ethanol<br>90% n-butane | Repellent for less than 1 week |
| A | 20% deet<br>4% polymer-1<br>16% ethanol<br>60% n-butane | Repellent over a 3-week period |
| B | 20% deet<br>4% polymer-2<br>16% ethanol<br>60% n-butane | Repellent to mildly repellent over a 3-week period |
| C | 20% deet<br>4% polymer-3<br>16% ethanol<br>60% n-butane | Repellent over a 3-week period |
| D | 5% deet<br>1% polymer-1<br>4% ethanol<br>90% n-butane | Repellent over a 3-week period |
| E | 5% deet<br>1% polymer 2<br>4% ethanol<br>90% n-butane | Repellent at time zero, neutral to mildly repellent for three weeks |
| F | 5% deet<br>1% polymer-3<br>4% ethanol<br>90% n-butane | Repellent at time zero, mildly repellent to repellent for three weeks |

[1] Polymer-1 contains about 50 mole percent maleic anhydride, about 25 mole percent of 1-decene and about 25 mole percent of 1-octadecene. Polymer-2 contains about 50 mole percent maleic anhydride, about 25 mole percent of 1-decene and about 25 mole percent of a mixture of alpha olefins consisting of about 50.1 mole percent of 1-eicosene, about 43.4 mole 1-docosene and about 6.5 mole percent of 1-tetracosene. Polymer-3 consists of about 50 mole percent maleic anhydride and about 50 mole percent 1-decene.
[2] *Blattella germanica* cockroaches.

TABLE 2

| Formula | Ingredients and Concentration[1] | Repellency Effect Against German Cockroaches[2] |
|---|---|---|
| Control-1 | 5% deet<br>5% ethanol<br>90% n-butane | 1 hour: repellent<br>1 week: neutral<br>2 weeks: —<br>3 weeks: — |
| G | 2% deet<br>0.4% polymer-1<br>1.6% ethanol<br>96% n-butane | 1 hour: repellent<br>1 week: mildly repellent<br>2 weeks: mildly repellent<br>3 weeks: neutral |
| H | 2% deet<br>1% polymer-1<br>4% ethanol<br>93% n-butane | 1 hour: repellent<br>1 week: neutral<br>2 weeks: —<br>3 weeks: — |
| I | 5% deet<br>0.4% polymer-1<br>1.6% ethanol<br>93% n-butane | 1 hour: repellent<br>1 week: mildly repellent<br>2 weeks: neutral<br>3 weeks: — |
| J | 5% deet<br>1% polymer-1<br>4% ethanol<br>90% n-butane | 1 hour: repellent<br>1 week: mildly repellent<br>2 weeks: mildly repellent<br>3 weeks: neutral |

[1] Polymer-1 consists of about 50 mole percent maleic anhydride, about 25 mole percent 1-decene and about 25 mole percent 1-octadecene.
[2] *Blattella germanica* cockroaches.

As shown in Table 1, the residual activity of deet was extended by the addition of the polymers of the invention as compared with a control formula not containing a polymer of this invention. The enhanced residual activity was observed at a weight ratio of insect repellent to polymer of about 5:1.

As shown in Table 2, the residual activity of deet was also extended by the addition of a polymer of this invention as compared with a deet formulation not containing a polymer of this invention. Enhanced residual activity occurred for all formulas having an insect repellent to polymer ratio of at least about 5:1. When this ratio was below about 5:1, as shown in Formula H, which had a ratio of insect repellent to polymer of about 2:1, enhanced residual activity was not observed when compared to Formula G, which had a ratio of 5:1 and contained the same concentration of insect repellent.

EXAMPLE 2

Butyl hydroxy anisole has also been discovered to be a good repellent for German cockroaches, *Blattella germanica*, but also lacking in functional residual repellent activity. To test the residual activity of the formulations of this invention, butyl hydroxy anisole was mixed with the polymer shown in Table 3, and tested for cockroach repellency by the following method.

Two one-pint paperboard containers, one treated and the other untreated were used to determine repellency. This allowed the cockroaches the choice between treated and untreated areas. The treated containers, containing 4 holes, each ½" in diameter, were coated with the formulas and the application rates shown in Table 3. The control formulas contained BHA without a polymer of the invention.

TABLE 3

| Formula | Ingredients and Concentration | Application Rate[4] | Repellency against German cockroaches[5] | | | |
|---|---|---|---|---|---|---|
| | | | 90% | 80% | 70% | 50% |
| Control-2 | 6.67% BHA[1] 93.33% ethanol | 1.0 mg BHA/cm$^2$ | 8 | 11 | 14 | 22 |
| Control-3 | 3.34% BHA 96.66% ethanol | 0.5 mg BHA/cm$^2$ | 2 | 5 | 7 | 15 |
| Control-4 | 0.67% BHA 99.33% ethanol | 0.1 mg BHA/cm$^2$ | 2 | 3 | 4 | 7 |
| K | 5% BHA 0.5% polymer-1[2] 94.5% ethanol | 0.645 mg BHA/cm$^2$ 0.065 mg P-1/cm$^2$ | 8 | 12 | 15 | 19 |
| L | 10% BHA 1% polymer-1 9% ethanol 80% propellent[3] | 0.217 mg BHA/cm$^2$ 0.022 mg P-1/cm$^2$ | 3 | 9 | 9 | 14 |

[1]BHA = butyl hydroxy anisole.
[2]Polymer-1 consists of about 50 mole percent maleic anhydride, about 25 mole percent 1-decene and about 25 mole percent 1-octadecene.
[3]The propellent consists of 80% isobutane and 20% propane.
[4]P-1 denotes polymer-1 shown in footnote 2.
[5]Repellent efficacy was based on the time, in days, that the repellency index remained at or above the designated percent repellency.

The harborages were placed in an plastic arena approximately 120 square inches by 4 inches deep, with greased side walls. Food and water were available to the 50 male cockroaches utilized in each test.

The containers were evaluated daily and the percent repellency was determined by recording the number of cockroaches under the treated and untreated containers and employing the following index.

$[(U-T)/(U+T)] \times 100 = \%$ repellency, wherein U is the number of cockroaches under the untreated container and T, the number under the treated container. All results represent the average of 4 test replications. The results are shown as the number of days that the repellency index remains at or above a certain percent repellency.

As the Table 3 results indicate, the addition of a polymer of this invention to the BHA formulations enhanced their residual activity against German cockroaches when compared to control formulations not containing the polymers of this invention. In this particular case, the formulations of this invention provided equivalent or superior residual activities at application rates that were considerably reduced over control formulations not containing a polymer of the invention.

Similar results are obtained when Formulas 1-10 are substituted for the test compositions in Examples 1 and 2.

This invention is not to be limited except as set forth in the following claims.

What is claimed is:

1. A volatile contact insect-repellent composition, which is effective against cockroaches and other crawling insects and which possesses enhanced residual insect repellent activity, comprising:
   (1) at least one volatile contact insect repellent; and
   (2) an effective amount of at least one polymer for prolonging residual activity of the insect repellent, said one polymer consisting of:
      (a) about 49-60 mole percent maleic anhydride and
      (b) about 51-40 mole percent of at least one 1-alkene having 4-30 carbon atoms.

2. A composition according to claim 1, wherein the polymer consists of:
   (a) about 49-55 mole percent maleic anhydride, and
   (b) about 45-51 mole percent of at least one 1-alkene having from 6-16 carbon atoms.

3. A composition according to claim 2, wherein the 1-alkene has from 8-12 carbon atoms.

4. A composition according to claim 1, wherein the polymer consists of about 49-55 mole percent maleic anhydride and about 45-51 mole percent of 1-decene.

5. A composition according to claim 1, wherein the polymer has:
   about 10-40 mole percent of at least one 1-alkene having from 4-16 carbon atoms, and about 10-40 mole percent of at least one 1-alkene having from 18-30 carbon atoms.

6. A composition according to claim 1, wherein the polymer consists of:
   (a) about 49-55 mole percent maleic anhydride,
   (b) about 20-30 mole percent of at least one 1-alkene having from 8-12 carbon atoms, and
   (c) about 20-30 mole percent of at least one 1-alkene having from 18-24 carbon atoms.

7. A composition according to claim 1, wherein the polymer consists of:
   (a) about 49-55 mole percent maleic anhydride,
   (b) about 20-30 mole percent 1-decene, and
   (c) about 20-30 mole percent 1-octadecene.

8. A composition according to claim 1, wherein the polymer consists of:
   (a) about 49-55 mole percent maleic anhydride, (b) about 20–30 mole percent of at least one 1-alkene having from 8–12 carbon atoms, and
(c) about 20–30 mole percent of a mixture of 1-alkenes consisting of about 45–55 mole percent 1-eicosene, about 40–55 mole percent 1-docosene, and about 5–10 mole percent 1-tetracosene.

9. A composition according to claim 1, wherein the volatile contact insect repellent is selected from the group consisting of N,N-diethyl toluamide; citronellal; citronellol; geraniol; nerol; linalool; butyl hydroxy anisole; and mixtures thereof.

10. A composition according to claim 1, wherein the insect repellent is selected from the group consisting of N,N-diethyl toluamide, butyl hydroxy anisole, and mixtures thereof.

11. A composition according to claim 1, wherein the volatile contact insect repellent is N,N-diethyl toluamide and the polymer consists of about 50 mole percent maleic anhydride and about 50 mole percent 1-decene.

12. A volatile contact insect-repellent composition, which is effective against cockroaches and other crawling insects and which possesses enhanced residual insect repellant activity, comprising:
(1) at least one volatile contact insect repellent;
(2) an effective amount of at least one polymer for prolonging residual activity of the insect repellent, said one polymer consisting of:
(a) about 49–60 mole percent maleic anhydride, and
(b) about 51–40 mole percent of at least one 1-alkene having 4–30 carbon atoms, and;
(3) a lower alkanol.

13. A composition accoridng to claim 12, wherein the polymer has:
about 10–40 mole percent of at least one 1-alkene having from 4–16 carbon atoms, and about 10–40 mole percent of at least one 1-alkene having from 18–30 carbon atoms.

14. A composition according to claim 1, wherein the volatile contact insect repellent is butyl hydroxy anisole and the polymer consists of about 50 mole percent maleic anhydride, about 25 mole percent 1-decene and about 25 mole percent 1-octadecene.

15. A composition according to claim 1, wherein the weight ratio of insect repellent to polymer is about 5:1 to about 50:1.

16. A method for repelling crawling insects such as cockroaches and the like, comprising applying an insect repellent composition to an area to be made crawling-insect repellent, said composition having enhanced residual repellent activity and comprising:
(1) at least one volatile contact insect repellent; and
(2) an effective amount of at least one polymer for prolonging residual activity of the insect repellent, said one polymer consisting of:
(a) about 49–60 mole percent maleic anhydride, and
(b) about 51–40 mole percent of at least one 1-alkene having 4–30 carbon atoms.

17. A method according to claim 16, wherien the polymer consists of:
(a) about 49–55 mole percent maleic anhydride, and
(b) about 45–51 mole percent of at least one 1-alkene having from 6–16 carbon atoms.

18. A method according to claim 17, wherein the 1-alkene has from 8–12 carbon atoms.

19. A method according to claim 16, wherein the polymer consists of about 49–55 mole percent maleic anhydride and about 45–51 mole percent of 1-decene.

20. A method according to claim 16, wherein the polymer has:
about 10–40 mole percent of at least one 1-alkene having from 4–16 carbon atoms, and about 10–40 mole percent of at least one 1-alkene having from 18–30 carbon atoms.

21. A method according to claim 16, wherein the polymer consists of:
(a) about 49–55 mole percent maleic anhydride,
(b) about 20–30 mole percent of at least one 1-alkene having from 8–12 carbon atoms, and
(c) about 20–30 mole percent of at least one 1-alkene having from 18–24 carbon atoms.

22. A method according to claim 16, wherein the polymer consists of:
(a) about 49–55 mole percent maleic anhydride,
(b) about 20–30 mole percent 1-decene, and
(c) about 20–30 mole percent 1-octadecene.

23. A method according to claim 16, wherein the polymer consists of:
(a) about 49–55 mole percent maleic anhydride,
(b) about 20–30 mole percent of at least one 1-alkene having from 8–12 carbon atoms, and
(c) about 20–30 mole percent of a mixture of 1-alkenes consisting of about 45–55 mole percent 1-eicosene, about 40–55 mole percent 1-docosene, and about 5–10 mole percent 1-tetracosene.

24. A method according to claim 16, wherein the volatile contact insect repellent is selected from the group consisting of N,N-diethyl toluamide; citronellal; citronellol; geraniol; nerol; linalool; butyl hydroxy anisole; and mixtures thereof.

25. A method according to claim 16, wherein the insect repellent is selected from the group consisting of N,N-diethyl toluamide, butyl hydroxy anisole and mixtures thereof.

26. A method for repelling crawling insects such as cockroaches and the like, comprising applying a volatile contact insect repellent composition to an area to be made crawling-insect repellent, said composition having enhanced residual repellent activity and comprising:
(1) at least one volatile contact insect repellent; and
(2) an effective amount of at least one polymer for prolonging residual activity of the insect repellent, said one polymer consisting of:
(a) about 49–60 mole percent maleic anhydride, and
(b) about 51–40 mole percent of at least one 1-alkene having 4–30 carbon atoms; and
(c) a lower alkanol.

27. A method according to claim 26, wherein the polymer has:
about 10–40 mole percent of at least one 1-alkene having from 4–16 carbon atoms, and about 10–40 mole percent of at least one 1-alkene having from 18–30 carbon atoms.

28. A method according to claim 16, wherein the weight ratio of insect repellent to polymer is about 5:1 to about 50:1.

29. A method according to claim 26, wherein the weight ratio of insect repellent to polymer is about 5:1 to about 50:1.

* * * * *